United States Patent
Smith et al.

(10) Patent No.: US 6,530,888 B2
(45) Date of Patent: Mar. 11, 2003

(54) IMAGING PROBES AND CATHETERS FOR VOLUMETRIC INTRALUMINAL ULTRASOUND IMAGING

(75) Inventors: Stephen W. Smith, Durham, NC (US); Edward D. Light, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 09/916,380

(22) Filed: Jul. 27, 2001

(65) Prior Publication Data

US 2002/0013529 A1 Jan. 31, 2002

Related U.S. Application Data

(62) Division of application No. 09/546,721, filed on Apr. 11, 2000, which is a division of application No. 09/074,907, filed on May 8, 1998, now Pat. No. 6,066,096.

(51) Int. Cl.[7] .................................................. A61B 8/12
(52) U.S. Cl. ...................... 600/463; 128/916
(58) Field of Search .................... 600/43, 463, 462, 600/466–467, 471, 380; 607/122; 128/916

(56) References Cited

U.S. PATENT DOCUMENTS

| | | | |
|---|---|---|---|
| 4,671,293 A | 6/1987 | Shaulov | 128/660 |
| 4,747,192 A | 5/1988 | Rokurota | 29/25.36 |
| 4,802,487 A | 2/1989 | Martin et al. | 128/662.06 |
| 4,870,867 A | 10/1989 | Shaulov | 73/625 |
| 4,887,605 A | 12/1989 | Angelsen et al. | 128/660.03 |
| 5,091,893 A | 2/1992 | Smith et al. | 367/153 |

(List continued on next page.)

OTHER PUBLICATIONS

Davidsen et al., "Two–Dimensional Arrays for Medical Ultrasound Using Multilayer Flexible Circuit Interconnection," *IEEE Transactions on Ultrasonics, Ferroelectrics, and Frequency Control*, vol. 45, No. 2, Mar. 1998.

Davidsen et al., "Two–Dimensional Random Arrays for Real Time Volumetric Imaging," *Ultrason. Imag.*, vol. 16, pp. 143–163, 1994.

Evans et al., "Arterial Imaging with a New Forward–Viewing Intravascular Ultrasound Catheter, I, Initial Studies," *Circulation*, vol. 89, No. 2, pp. 712–717, Feb. 1994.

Light et al., "Advances in Two Dimensional Arrays for Real Time Volumetric Imaging," *1997 IEEE Ultrasonics Symposium*, pp. 1619–1623, 1997.

Ng et al., "Arterial Imaging With a New Forward–Viewing Intravascular Ultrasound Catheter, II, Three–Dimensional Reconstruction and Display of Data," *Circulation*, vol. 89, No. 2, pp. 718–723, Feb. 1994.

Piel, Jr., "7.5 MHz Pediatric Phased Array Transesophageal Endoscope," *1994 Ultrasonics Symposium*, pp. 1527–1530, 1994.

Seward et al., "Ultrasound Cardioscopy: Embarking on a New Journey," *Mayo Clin. Proc.*, vol. 71, No. 7, pp. 629–635, Jul. 1996.

Smith, et al., "Two–Dimensional Arrays for Medical Ultrasound," *Ultrasonic Imaging*, vol. 14, pp. 213–233, 1992.

*Primary Examiner*—Francis J. Jaworski
(74) *Attorney, Agent, or Firm*—Myers Bigel Sibley & Sajovec

(57) ABSTRACT

A real time three dimensional ultrasound imaging probe apparatus is configured to be placed inside a body. The apparatus comprises an elongated body having proximal and distal ends with an ultrasonic transducer phased array connected to and positioned on the distal end of the elongated body. The ultrasonic transducer phased array is positioned to emit and receive ultrasonic energy for volumetric forward scanning from the distal end of the elongated body. The ultrasonic transducer phased array includes a plurality of sites occupied by ultrasonic transducer elements. At least one ultrasonic transducer element is absent from at least one of the sites, thereby defining an interstitial site. A tool is positioned at the interstitial site. In particular, the tool can be a fiber optic lead, a suction tool, a guide wire, an electrophysiological electrode, or an ablation electrode. Related systems are also discussed.

11 Claims, 11 Drawing Sheets

U.S. PATENT DOCUMENTS

| | | |
|---|---|---|
| 5,178,150 A | 1/1993 | Silverstein et al. .... 128/662.06 |
| 5,273,045 A | 12/1993 | Chihara et al. ........ 128/662.06 |
| 5,278,757 A * | 1/1994 | Hoctor et al. ................ 600/443 |
| 5,287,330 A | 2/1994 | Gilmour ...................... 367/103 |
| 5,320,104 A * | 6/1994 | Fearnside et al. ............ 600/447 |
| 5,335,663 A | 8/1994 | Oakley et al. ............... 128/662 |
| 5,373,845 A | 12/1994 | Gardineer et al. ..... 128/660.09 |
| 5,421,338 A | 6/1995 | Crowley et al. ........ 128/662.06 |
| 5,437,283 A | 8/1995 | Ranalletta et al. ..... 128/662.06 |
| 5,488,954 A | 2/1996 | Sleva et al. ............. 128/662.03 |
| 5,493,541 A | 2/1996 | Snyder ....................... 367/155 |
| 5,522,393 A | 6/1996 | Phillips et al. ......... 128/661.09 |
| 5,617,865 A | 4/1997 | Palczewska et al. ........ 600/459 |
| 5,644,085 A | 7/1997 | Lorraine et al. ............... 73/641 |
| 5,651,366 A | 7/1997 | Liang et al. ........... 128/662.06 |
| 5,655,270 A | 8/1997 | Pattanyak et al. .......... 29/25.35 |
| 5,699,805 A * | 12/1997 | Seward et al. ............... 600/459 |
| 5,704,361 A * | 1/1998 | Seward et al. ............... 128/916 |
| 5,715,825 A | 2/1998 | Crowley ................ 128/602.06 |
| 5,744,898 A | 4/1998 | Smith et al. ................. 310/334 |
| 5,749,833 A | 5/1998 | Hakki et al. ................. 600/380 |
| 5,774,960 A | 7/1998 | De Fraguier et al. ...... 29/25.35 |
| 5,829,439 A | 11/1998 | Yokosawa et al. ..... 128/662.06 |
| 5,840,031 A | 11/1998 | Crowley ..................... 600/440 |
| 5,938,612 A | 8/1999 | Kline-Schoder et al. .... 600/459 |
| 6,019,727 A | 2/2000 | Koger et al. ................. 600/459 |
| 6,059,728 A * | 5/2000 | Ritter ......................... 600/443 |
| 6,066,096 A * | 5/2000 | Smith et al. ................. 600/439 |
| 6,171,247 B1 * | 1/2001 | Seward et al. ............... 600/459 |

* cited by examiner

IMAGING PROBES AND CATHETERS FOR VOLUMETRIC INTRALUMINAL ULTRASOUND IMAGING

CLAIM FOR PRIORITY

This application is a divisional of U.S. patent application Ser. No. 09/546,721, filed on Apr. 11, 2000, which was a divisional of U.S. patent application Ser. No. 09/074,907 filed on May 8, 1998, which issued as U.S. Pat. No. 6,066,096 on May 23, 2000, the disclosures of which are incorporated herein by reference.

This invention was made with Government support under grant number CA56475 from the National Institute of Health. The Government has certain rights to this invention.

FIELD OF THE INVENTION

The present invention relates to the field of imaging in general and to ultrasound imaging in particular.

BACKGROUND OF THE INVENTION

Ultrasonic imaging has been applied in many two dimensional systems using pulse echo B-mode tomography or B-scans. These systems display echoes returning to an ultrasonic transducer as brightness levels proportional to echo amplitude. The brightness levels may be used to create cross-sectional images of the object in the plane perpendicular to the transducer aperture.

Examination of objects in three dimensions has evolved using a number of modalities including x-ray, ultrasound, and nuclear magnetic resonance. In particular, improvements have been made in spatial resolution, dynamic range, display methods and data analysis. For example, ultrasound scanning of three-dimensional objects by sequential B-scans followed by off-line reconstruction and display of rendered images has progressed in recent years with the introduction of commercial three-dimensional systems. Off-line rendering, however, may take several minutes to produce a single three-dimensional scan.

In the area of high-speed three-dimensional ultrasound imaging, U.S. Pat. No. 4,596,145 to Smith and von Ramm discloses an acoustic imaging system capable of producing high-speed projection orthoscopic images, as well as a single high-speed C-scan image using a two-dimensional array transducer and receive mode parallel processing. The C-scan image may be defined as a planar section of the object parallel to the effective transducer aperture. In 1987, U.S. Pat. No. 4,694,434 to von Ramm and Smith disclosed a steered array acoustic imaging scanner capable of producing a high-speed pyramidal scan to obtain a volumetric (three-dimensional) image using a two-dimensional array transducer and receive mode parallel processing.

High frequency intraluminal ultrasound imaging probes have been developed, including circular arrays and mechanically steered transducers. The circular arrays and mechanically steered transducers produce B-mode circular side scan geometries in which the ultrasound beam is swept through a 360° arc. The 360° arc may create a high-speed circular image within a vessel or lumen with a maximum range of approximately one centimeter. For example, U.S. Pat. No. 3,938,502 to Bom and U.S. Pat. No. 4,917,097 to Proudian, et al. disclose circular arrays of transducer elements within a catheter to produce a circular side scanning intraluminal B-mode image. U.S. Pat. No. 4,794,931 to Yock and U.S. Pat. No. 5,243,988 to Sieben, et al. disclose motor-driven piston transducers at the end of the catheters to produce circular side scanning intervascular imaging.

Catheters may be used in conjunction with the systems described above to provide intraluminal imaging. Intraluminal imaging may involve inserting a catheter, that includes an ultrasonic transducer phased array, into coronary vessels, pulmonary arteries, the aorta, or venous structures. For example, U.S. Pat. No. 5,704,361 to Seward, et al. discloses a volumetric imaging ultrasound transducer under-fluid catheter system. The advantages of Seward may, however, be limited by the quality of the imaging provided therein. In particular, the catheter probes disclosed in Seward show the therapeutic tools adjacent to the transducer array on the catheter tip, thereby reducing the area available for the transducer array. Such an array may provide images having reduced spatial resolution. Moreover, the applications described in Seward may be limited to procedures involving catheters.

The catheters described above may be combined with electrodes or tools to locate (cardiac electrophysiological mapping) and perform therapy on (radiofrequency ablation) or monitor tissue. For example, a three-dimensional ultrasound imaging device using a catheter may be combined with an ablation electrode to provide therapy to particular tissue. The therapy provided by the electrode, however, may be limited by the registration between the image provided by the catheter and the electrodes associated with the catheter. For example, a user may have difficulty translating the image produced by the catheter to the position of the electrode, thereby possibly creating difficulty in applying the electrode to the intended tissue. Moreover, the electrode may obscure the three dimensional ultrasound image when the electrode is within the field of view of the image.

In view of the above discussion, there exists a need to improve the quality of real-time three-dimensional imaging in intraluminal ultrasound applications.

SUMMARY OF THE INVENTION

In view of the above discussion, it is an object of the present invention to provide improved ultrasonic imaging probes.

It is another object of the present invention to provide improved therapy in conjunction with ultrasonic imaging.

These and other objects are provided by a real time three dimensional ultrasound imaging probe configured to be placed inside a body. The imaging probe includes an elongated body having proximal and distal ends. An ultrasonic transducer phased array is connected to and positioned on the distal end of the elongated body. The ultrasonic transducer phased array is configured to emit ultrasonic energy for volumetric scanning from the distal end of the elongated body and receive reflected ultrasonic energy. The ultrasonic transducer phased array includes a plurality of sites occupied by ultrasonic transducer elements. At least one ultrasonic transducer element is absent from at least one of the sites, thereby defining an interstitial site. A tool is positioned at the interstitial site. In particular, the tool can be a fiber optic lead, a suction tool, a scalpel, a guide wire, an electrophysiological electrode, or an ablation electrode. Positioning the tool at an interstitial site allows a large ultrasonic transducer phased array aperture, thereby producing superior image resolution and sensitivity as compared to the prior art. Conventional probes may include tools, positioned outside the ultrasonic transducer phased array, that reduce the aperture size of the ultrasonic transducer phased array. A reduced aperture size provides lower image resolution and sensitivity. Positioning the tool within the ultrasonic transducer phased array allows the user to accurately align the tool with the tissue to be treated more accurately, thereby making the probe easier to use and more effective.

In one aspect, a plurality of ultrasonic transducer elements are absent from a plurality of sites, defining a plurality of interstitial sites. The plurality of interstitial sites have a circular arrangement within the ultrasonic transducer phased array. The circular arrangement allows a larger aperture size while limiting side lobe effects on the imaging.

In another aspect, the ultrasonic transducer elements are arranged in a row of ultrasonic transducer elements and a column of ultrasonic transducer elements, defining four quadrants of interstitial sites within the ultrasonic transducer phased array. The row of ultrasonic transducer elements is substantially perpendicular to the column of ultrasonic transducer elements. A tool can be positioned at an interstitial site within each quadrant of the ultrasonic transducer phased array.

In still another aspect, a real time three dimensional ultrasound imaging probe apparatus is configured to be placed inside a body. The apparatus includes an elongated body having proximal and distal ends with an ultrasonic transducer phased array connected to and positioned on the distal end of the elongated body. The ultrasonic transducer phased array is configured to emit either forward or side scanning ultrasonic energy for volumetric scanning from the distal end of the elongated body and receive reflected ultrasonic energy. An electrode assembly is connected to and overlies the ultrasonic transducer phased array, wherein the electrode assembly is transparent to ultrasonic energy.

The ultrasonically transparent electrode assembly allows the user to more accurately apply the electrode to tissue within a region of interest, thereby allowing a reduction in the complexity associated with the prior art. For example, the present invention allows the user to apply the electrode to the tissue by locating the tissue within the region of interest using the real time three dimensional images. In contrast, users of some conventional imaging probes locate the tissue and then manipulate an electrode to the tissue by understanding the registration between the image and the physical location of the electrode on the probe.

The present invention also provides increased image resolution and sensitivity (signal to noise ratio) by increasing the aperture size of the ultrasonic transducer phased array to include a majority of the surface area of the distal end of elongated body. In particular, conventional ultrasonic transducer phased arrays cover a minority of the distal end of the elongated body described therein. Moreover, the prior art generally discloses an ultrasonic transducer phased array in conjunction with conventional tools and electrodes positioned in close proximity to the ultrasonic transducer phased array, thereby limiting the size of the ultrasonic transducer phased array. As a result, images produced by conventional imaging probes have less spatial resolution and sensitivity relative to those produced by the present invention.

The present invention also provides improved imaging over the prior art as applied to biopsy procedures. In particular, a real time three dimensional imaging biopsy apparatus configured to be inserted into a body includes an elongated body, having proximal and distal ends, that is configured to be extended through a biopsy needle into the body. An ultrasonic transducer phased array is connected to and positioned on the distal end of the elongated body. The ultrasonic transducer phased array is configured to emit and receive ultrasonic energy for volumetric scanning from the distal end of the elongated body.

The present invention also provides improved imaging over the prior art as applied to minimally invasive surgical procedures. In particular, a real time three dimensional ultrasonic imaging probe apparatus configured to be placed into a body, includes a cannula configured to provide access to a cavity inside the body. An elongated body, having proximal and distal ends, is configured to extend into the body via the cannula. An ultrasonic transducer phased array is connected to and is positioned on the distal end of the elongated body. The ultrasonic transducer phased array is configured to emit ultrasonic energy for volumetric scanning from the distal end of the elongated body and receive reflected ultrasonic energy.

DETAILED DESCRIPTION OF THE INVENTION

The present invention will now be described more fully hereinafter with reference to the accompanying drawings, in which a preferred embodiment of the invention is shown. This invention may, however, be embodied in many different forms and should not be construed as limited to the embodiments set forth herein; rather these embodiments are provided so that this disclosure will be thorough and complete, and will fully convey the scope of the invention to those skilled in the art. Like numbers refer to like elements throughout.

Figure 1:
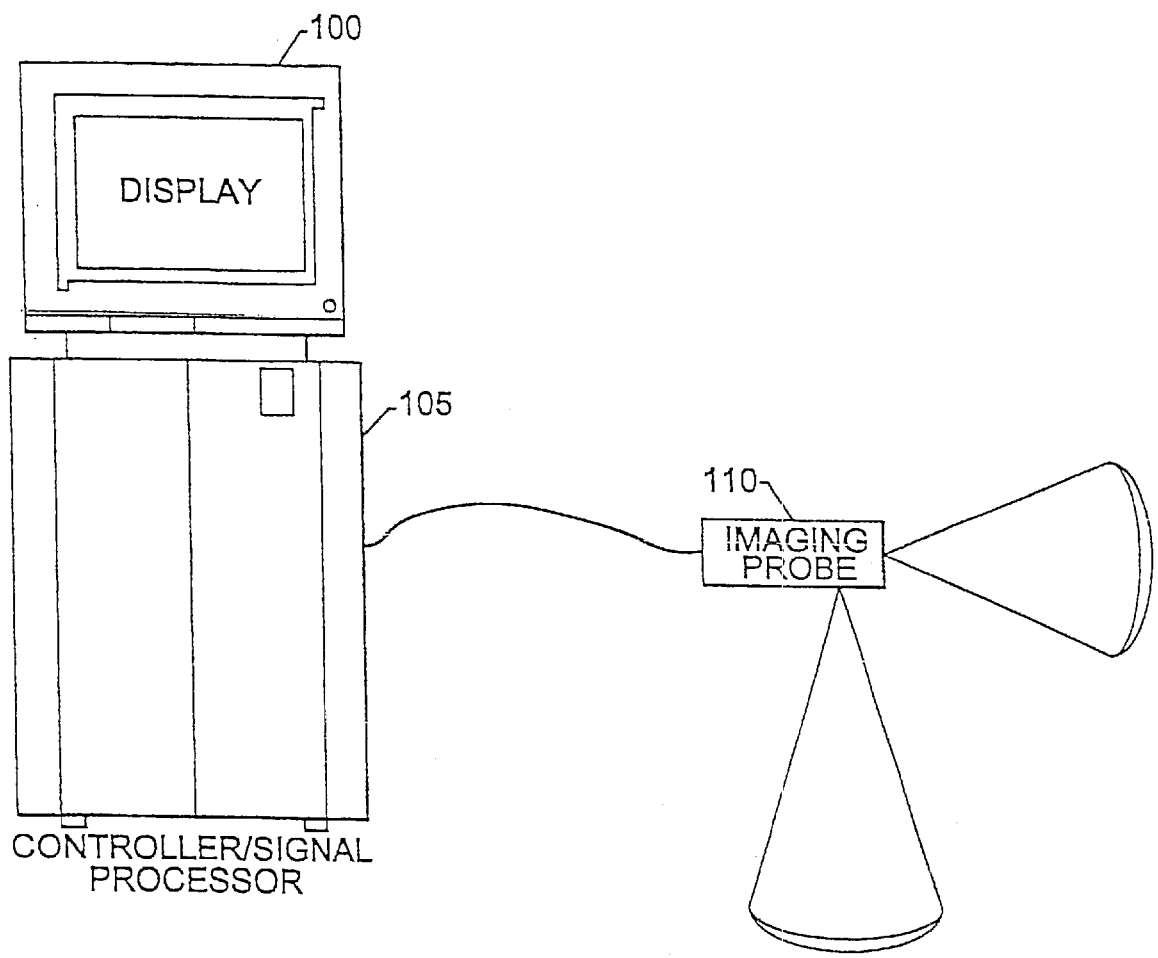
FIG. 1 is a block diagram of a real time three dimensional ultrasonic imaging system.

FIG. 1 is a block diagram of an ultrasonic imaging system that provides real time three dimensional ultrasonic images. The imaging probe 110 is a real time three dimensional imaging catheter, biopsy probe, surgical or endoluminal probe (such as arectal, prostrate, transurethal, or intravaginal probe) that can be configured to provide either forward or side scanning volumetric scanning ultrasonic energy via an ultrasonic transducer phased array under the control of the controller/signal processor 105. The imaging probe 110 can be inserted into a region of interest (such as a inside the body of a patient) to provide real time three dimensional ultrasonic imaging of objects within the region of interest. For example, the imaging probe 110 can be a real time three dimensional imaging catheter used to provide imaging during cardiac or prostrate procedures. Accordingly, the imaging catheter probe 110 would have a diameter in the range between about 3 French and 20 French. Alternately, the imaging probe 110 can provide imaging during needle biopsy or minimally invasive surgical procedures (such as in conjunction with a trocar during knee or abdominal surgery). Accordingly, the imaging probe would have a diameter in the range between about 1 millimeter (mm) and 20 mm. The imaging probe can include mechanical, surgical, and therapeutic tools (such as a suction tool, an optical fiber, a guide wire, or a scalpel blade) and electrodes to monitor or treat a particular tissue (such as electrophysiological or ablation electrodes). As described herein, a configuration for the emission of ultrasonic energy for volumetric scanning includes a configuration for the emission of volumetric forward scanning ultrasonic energy and a configuration for the emission of volumetric side scanning ultrasonic energy.

The controller/signal processor 105 transmits/receives electrical pulses to/from imaging probe 110. For example, the controller/signal processor 105 transmits electrical pulses to the imaging probe 110 that cause the ultrasonic transducer phased array to emit ultrasonic energy. The controller/signal processor also receives electrical pulses from the imaging probe 110 caused by the incidence of ultrasonic energy reflected from objects within the region of interest upon the ultrasonic transducer phased array. The controller/signal processor 105 provides a volumetric image on the display 100 of the object within the region of interest based on the electrical pulses received from the imaging probe 110. For example, the image may be formed using the systems and techniques disclosed in U.S. Pat. No. 5,546,807 to Oxaal et al. entitled High Speed Volumetric Ultrasound Imaging System. The display can be a cathode ray tube, liquid crystal display, or other device with suitable dynamic range for the display of volumetric images.

Figure 2A:
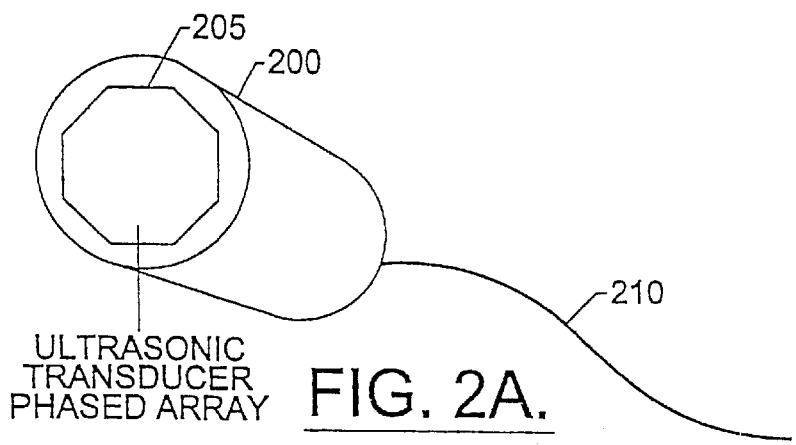
FIG. 2A is an enlarged partial perspective view an imaging probe configured to emit and receive ultrasonic energy for volumetric forward scanning according to the present invention.
Figure 2B:
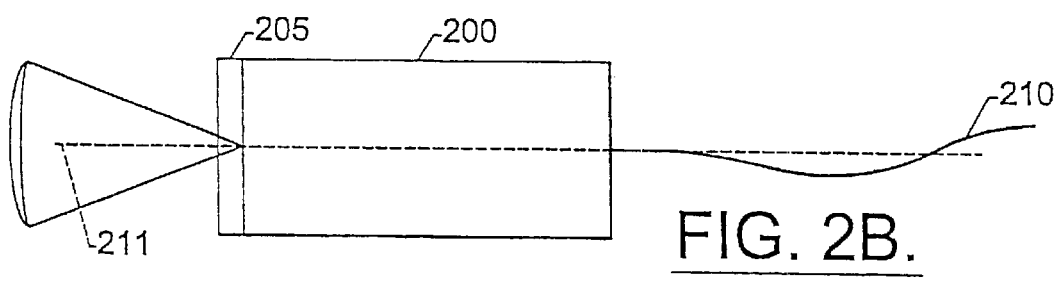
FIG. 2B is an enlarged side view of an imaging probe of FIG. 2A.

FIGS. 2A and 2B are enlarged partial perspective and side views of an imaging probe 110 configured to emit and receive ultrasonic energy for volumetric forward scanning according to the present invention. The imaging probe includes an elongated body 200 having proximal and distal ends. The ultrasonic transducer phased array 205 is connected to and positioned on the distal end of the elongated body 200, and positioned to emit and receive ultrasonic energy for volumetric forward scanning from the distal end of the elongated body 200. Imaging is provided by inserting the imaging probe into the region of interest (such as the body of a patient) so that the ultrasonic energy emitted from the ultrasonic transducer phased array is incident upon and is reflected from an object within the region of interest (such as tissue). The term body, as used herein, includes a biological entity, such as a human body, animal body, or vessel or container filled with fluid or airborne media subject to non-destructive evaluation (such as a nuclear reactor vessel).

The cable 210 provides a plurality of conductors (such as wires or optical fibers) for transmission of signals to/from the controller/signal processor 105. In one embodiment, the cable 210 includes 70 conductors.

Figure 2C:
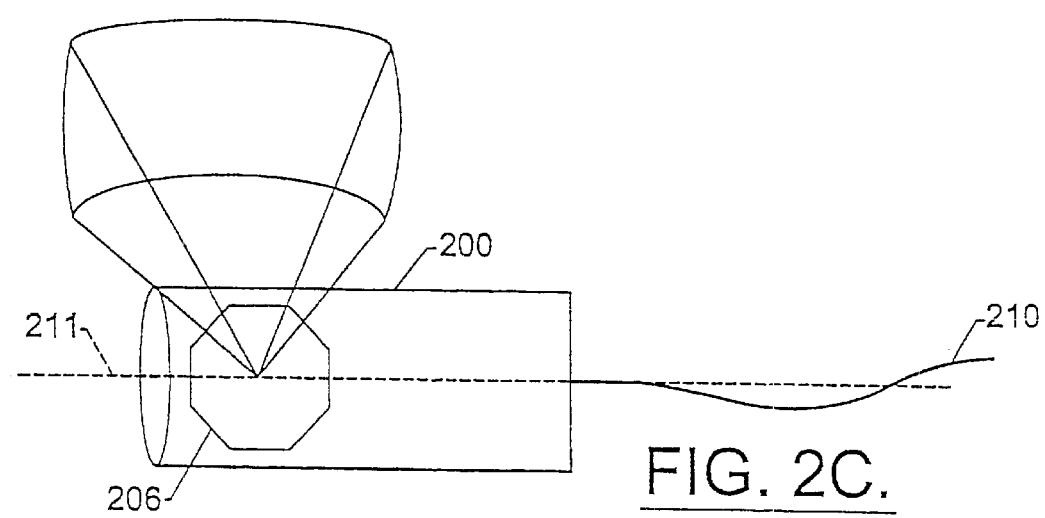
FIG. 2C is an enlarged partial perspective view an imaging probe configured to emit and receive ultrasonic energy for volumetric side scanning according to the present invention.
Figure 2D:
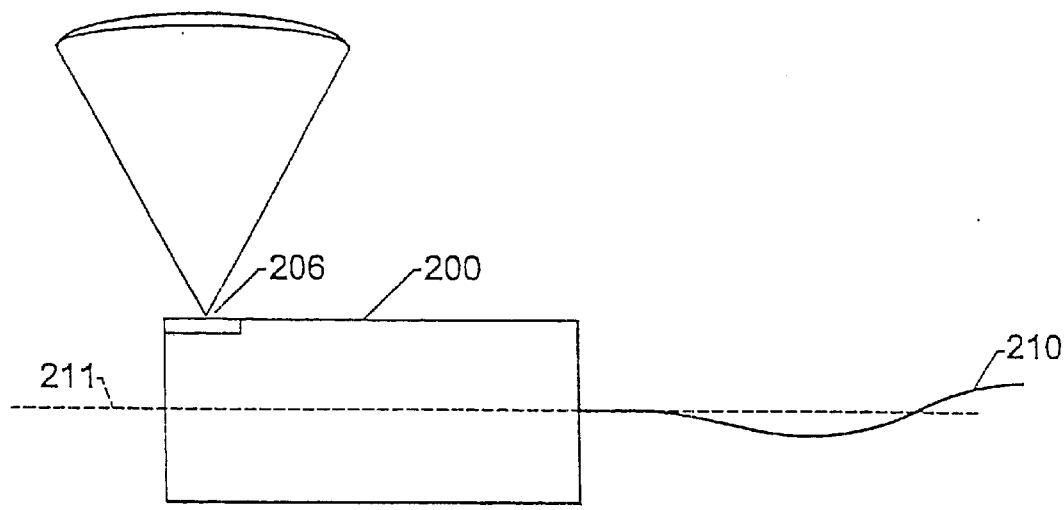
FIG. 2D is an enlarged side view of an imaging probe of FIG. 2C.

FIGS. 2C and 2D are enlarged partial perspective and side views of an imaging probe 110 configured to emit and receive ultrasonic energy for volumetric side scanning according to the present invention. Side scanning can provide a real time three dimensional image of objects located such that rotation of a forward scanning probe described above is less practical (such as a cardiac ventricular wall). The ultrasonic transducer phased array 206 is positioned substantially parallel to the longitudinal axis 211 of the elongated body 200 to provide side scanning ultrasonic energy. It should be understood that substantially parallel includes an orientation of the ultrasonic transducer phased array that is within +/−45 degrees of a completely parallel orientation.

Figure 2E:
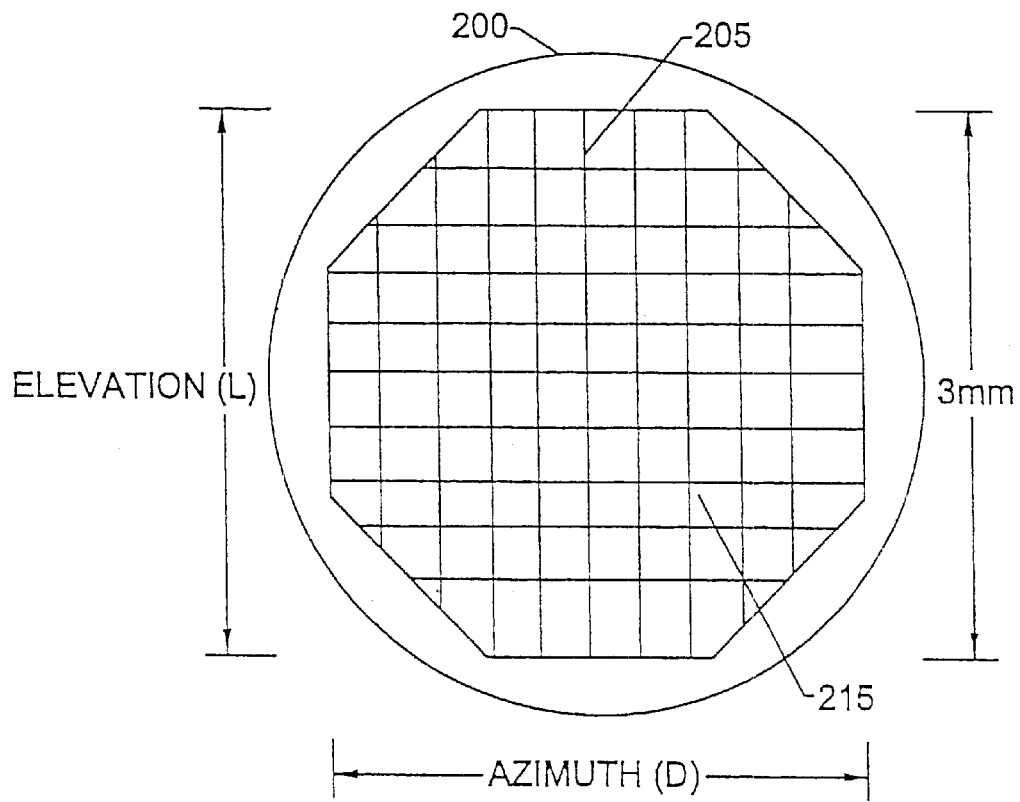
FIG. 2E is an enlarged view of elements of an ultrasonic transducer phased array according to the present invention.

FIG. 2E is an illustration of a preferred embodiment of an ultrasonic transducer phased array 205 connected to and positioned on the distal end of the elongated body 200 to emit volumetric forward or side scanning ultrasonic energy wherein the ultrasonic transducer phased array 205 covers a major portion of the distal end of the elongated body 200 (more than 50% of the distal end of the elongated body). The ultrasonic transducer phased array 205 is formed in an octagonal shape so as to increase the number of ultrasonic transducer elements included in the ultrasonic transducer phased array 205 positioned on the distal end of the elongated body. The ultrasonic transducer phased array operates at about 5 megahertz (MHz), includes 70 elements spaced about 0.2 mm apart, and is about 3 mm in diameter.

The ultrasonic transducer phased array 205 includes a plurality of ultrasonic transducer transmit and receive elements (elements) 215 arranged in row and column configuration. The elements can be arranged as a sparse array, a fully populated array (such as 10×10, 20×20, 60×60, 80×80), a Mills Cross array, a random distribution array, or a periodic distribution array. The ultrasonic transducer elements 215 receive electrical pulses from the controller/signal processor 105, as described above, causing the ultrasonic transducer elements 215 to emit ultrasonic energy. Furthermore, the ultrasonic transducer elements are provided with electrical pulses according to a phase sequence in the row and column direction as described in U.S. Pat. No. 5,546,807 to Oxaal et al. to produce the volumetric image described therein. The emitted ultrasonic energy is reflected from an object within the region of interest and is incident upon the elements 215 and thereby causing a corresponding electrical pulse to be transmitted to the controller/signal processor 105. The ultrasonic transducer phased array is made from a piezoelectric material.

The ultrasonic transducer phased array 205 is configured to cover a majority of the distal end of the elongated body 200 to provide a large aperture relative to the prior art. In particular, an ultrasonic transducer phased array 205 may provide superior resolution, $\theta_A$ (resolution in the azimuth dimension) and $\theta_E$ (resolution in the elevation dimension), by increasing the azimuth and elevation dimensions of the elongated body 200 allocated to the ultrasonic transducer phased array 205 according to:

$$\Theta_E = \sin^{-1}(\lambda/L) \quad \Theta_A = \sin^{-1}(\lambda/D)$$

where $\lambda$ is the wavelength of the ultrasonic energy and where L is the aperture size of the ultrasonic transducer phased array 205 in the elevation dimension and where D is the aperture size of the ultrasonic transducer phase array in the azimuth dimension. A larger aperture size also provides increased sensitivity (signal to noise ratio) in proportion to the improved resolution described above. For example, in contrast to the ultrasonic transducer phased arrays described herein, the ultrasonic transducer phased arrays disclosed in Seward cover a minority of the elongated body described therein. Moreover, Seward discloses an ultrasonic transducer phased array in conjunction with conventional tools and electrodes positioned in close proximity to and outside of the ultrasonic transducer phased array, thereby limiting the size of the ultrasonic transducer phased array. As a result, the images produced by the prior art may have low spatial resolution and sensitivity relative to those produced by the present invention. Moreover, the three dimensional ultrasound imaging of the prior art may be obscured when conventional tools are used within the field of view of the ultrasonic transducer phased array.

Figure 2F:
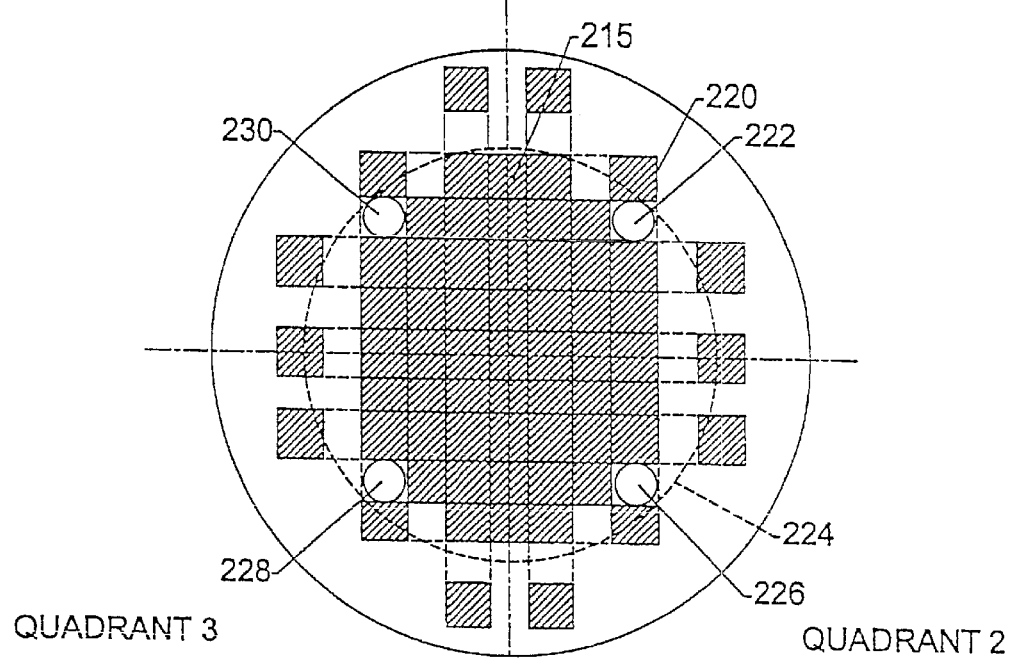
FIG. 2F is an enlarged view of elements of a sparsely populated periodic ultrasonic transducer phased array with tools according to the present invention.

FIG. 2F is an enlarged view of elements of a sparsely populated periodic ultrasonic transducer phased array with tools according to the present invention. The ultrasonic transducer phased array includes a plurality of sites occupied by ultrasonic transducer elements 215. The ultrasonic transducer phased array 205 is divided into four quadrants: quadrant 1, quadrant 2, quadrant 3, and quadrant 4. At least one of the ultrasonic transducer elements is absent from the ultrasonic transducer phased array, thereby defining an interstitial site. A tool can be positioned at the interstitial site to provide therapy to or monitoring of tissue. In a preferred embodiment, a plurality of ultrasonic transducer elements 215 are absent, thereby defining a plurality of interstitial sites having a circular arrangement 224 in which a plurality of tools can be positioned.

The circular arrangement 224 allows tools 222, 226, 228, and 230 to be positioned within the ultrasonic transducer phased array 205 and provides improved image resolution and sensitivity and reduces the effect of side lobes produced by smaller array dimensions as described above. The plurality of tools are distributed among the quadrants to reduce the side lobe effects caused by the presence of the tools. For example, tool 222 is positioned in quadrant 1, tool 226 is positioned in quadrant 2, tool 228 is positioned in quadrant 3, and tool 230 is positioned in quadrant 4. The tools may be a fiber optic lead, an ablation electrode, an electrophysiological electrode, a suction tool, or a guide wire. The inclusion of tools within the ultrasonic transducer phased array 205 allows the user to align the tool with the tissue more accurately, thereby making the imaging probe easier to use and more effective.

Figure 2G:
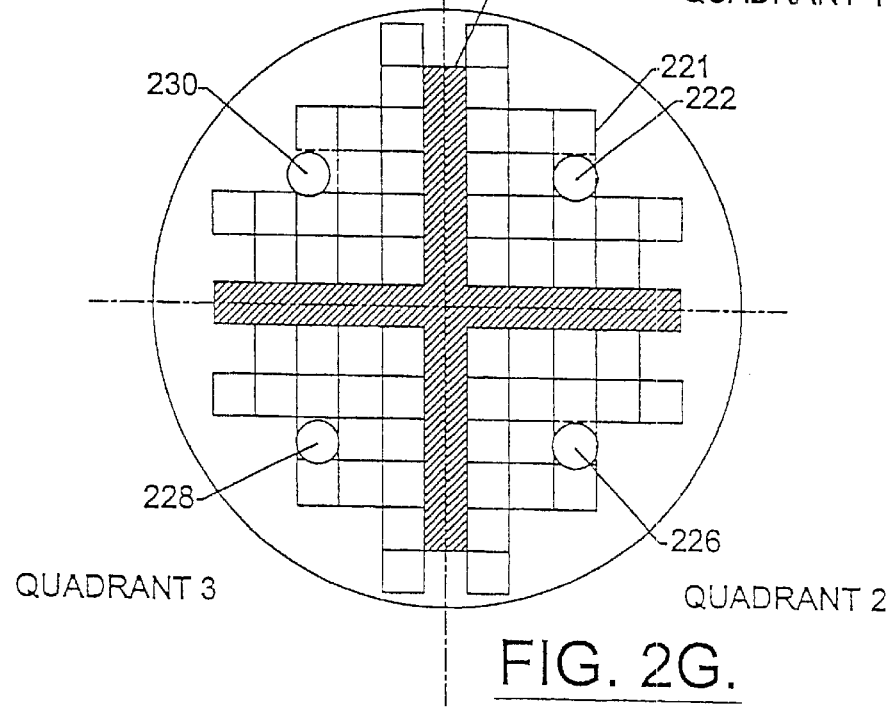
FIG. 2G is an enlarged view of a row of ultrasonic transducer elements and a column of ultrasonic transducer elements with tools according to the present invention.

FIG. 2G is an enlarged view of a row of ultrasonic transducer elements and a column of ultrasonic transducer elements (a Mills cross array) with tools according to the present invention. The combination of the row of ultrasonic transducer elements and the column of ultrasonic transducer elements define four quadrants of the ultrasonic transducer phased array: quadrant 1, quadrant 2, quadrant 3, and quadrant 4. The quadrants include a plurality of interstitial sites 221 from which ultrasonic transducer elements 215 are absent.

The sparse array may be implemented by selectively connecting a sub-set of conductors included in the cable 210 to corresponding elements 215. For example, a sparse array may be implemented using a single row and column of ultrasonic transducer elements in combination. The row and column ultrasonic transducer elements are provided with electrical pulses and receive mode delays according to the phasing described above. Alternately, the elements 215 within the ultrasonic transducer phased array 205 may be arranged according to a periodic distribution in which the spacing between transmit and receive elements is different so as to reduce grating lobe and side lobe effects. Another alternative distribution includes a random array geometry with a gaussian sampling of the transmit elements and a uniform sampling of the receive elements.

In one embodiment, tools 222, 226, 228, and 230 are positioned at interstitial sites in the quadrants 1, 2, 3, and 4 defined by the row and column of ultrasonic transducers. In a preferred embodiment, a single tool is positioned in each quadrant so as to minimize the effects of side lobes on the imaging. The tools may be a fiber optic lead, an ablation electrode, an electrophysiological electrode, a suction tool, or a guide wire. The inclusion of tool within the ultrasonic transducer phased array allows the user to align the tool with the tissue more accurately, thereby making the imaging probe easier to use and more effective.

Figure 3A:
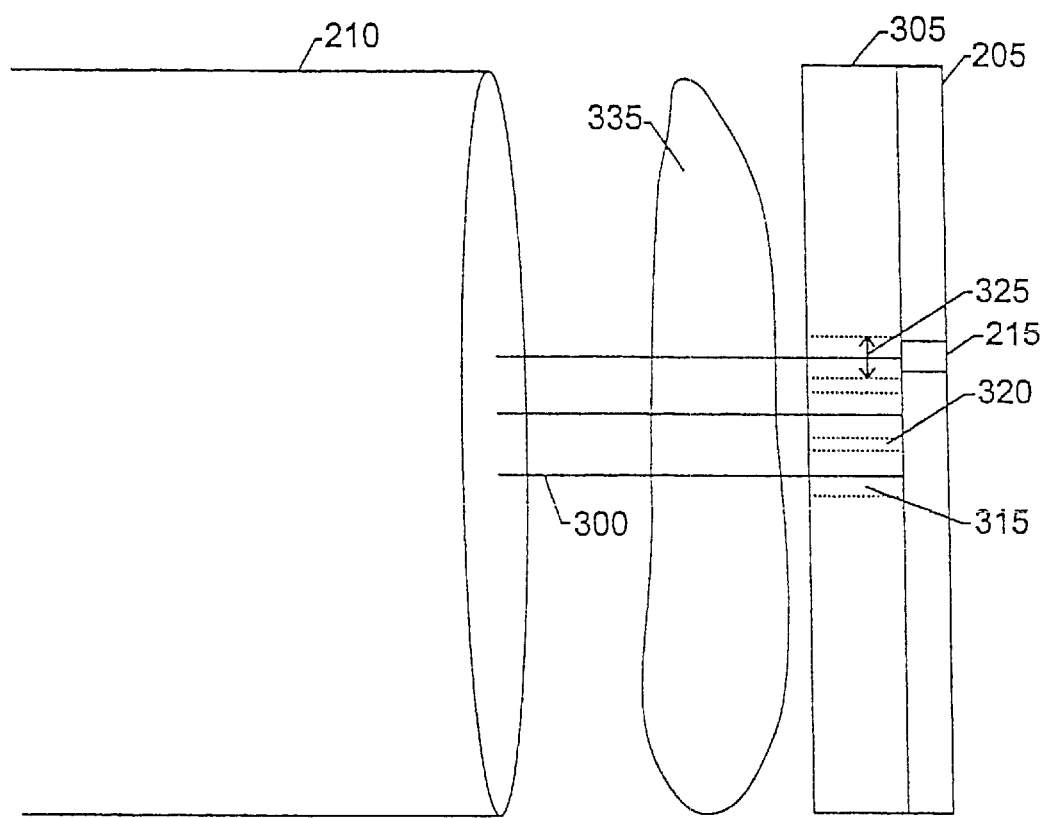
FIG. 3A is an enlarged cross-sectional view of a real time three dimensional imaging probe apparatus configured to emit and receive ultrasonic energy for volumetric forward scanning according to the present invention.

FIG. 3A is an enlarged cross-sectional view of a real time three dimensional imaging probe apparatus configured to emit volumetric forward scanning ultrasonic energy according to the present invention. A plurality of conductors 300 within the cable 210, having proximal and distal ends, are suitable for conducting electrical impulses to and from the corresponding elements 215 of the ultrasonic transducer phased array 205. The plurality of conductors 300 pass through a plurality of spaced holes 315 in the mounting plate 305 having a first and second side. The plurality of conductors 300 are connected to corresponding elements 215 within the ultrasonic transducer phased array 205 that is connected to and overlying the second side of the mounting plate 305.

A backing material 335 is positioned between the mounting plate 305 and the distal end of the elongated body 210. The acoustic impedance of the backing material 335 is matched to the acoustic impedance of the mounting plate 305 to reduce the amount of acoustic energy reflected back to the ultrasonic transducer phased array 205. The mounting plate 305 is made from a material which is acoustically transparent to ultrasonic energy at the resonant frequency of the ultrasonic transducer phased array 205. The term acoustically transparent, in the frequency band, includes materials that reflect a portion of an incident ultrasonic energy in the range between about 50% and 0% of the incident ultrasonic energy. For example, the mounting plate 305 can be a soft polymer material such as polyimide. In a preferred embodiment, the impedance of the mounting plate 305 is in the range between about 2 MRayls and 5 MRayls.

The plurality of holes 315 in the mounting plate 305 are spaced to accommodate the spacing of the elements 215 within the ultrasonic transducer phased array 205. In a preferred embodiment, the hole spacing 320 is about 0.2 mm on center and the hole diameter 325 is about 0.1 mm. In a preferred embodiment, the holes 315 are created using a $CO_2$ or excimer laser. The $CO_2$ or excimer laser can avoid over-stressing the mounting plate while the holes 315 are created and may be controlled with greater precision than can mechanical drilling. In one embodiment, the holes 315 are filled with a conductive epoxy. The plurality of conductors 300 are connected to the conductive epoxy. In another embodiment, the plurality of conductors 300 pass through the holes 315 and are connected to the plurality of corresponding elements 215. The holes 315 are then filled with the conductive epoxy.

In the prior art, mechanical drilling of holes with a diameter and spacing described above may over-stress the mounting plate material, thereby causing a failure of the mounting plate. Moreover, control and accuracy of a mechanical drilling process may be difficult at the dimensions described above. Furthermore, a drill bit capable of drilling a hole having a diameter of about 0.1 mm may be difficult to obtain and may be prone to failure.

The mounting plate 305 is formed to a thickness, D, that does not exceed $$D=\lambda$$

where $\lambda$ is the wavelength of the ultrasonic energy emitted by the ultrasonic transducer phased array. For example, for ultrasonic energy emitted at 5 MHz, the thickness of the mounting plate 305 should not exceed 0.075 mm. The thickness described above may provide additional structural integrity to the mounting plate 305. Consequently, the mounting plate 305 may be better suited to the creation of the holes 315 having the hole diameter 325 and the hole spacing 320 described above.

Figure 3B:
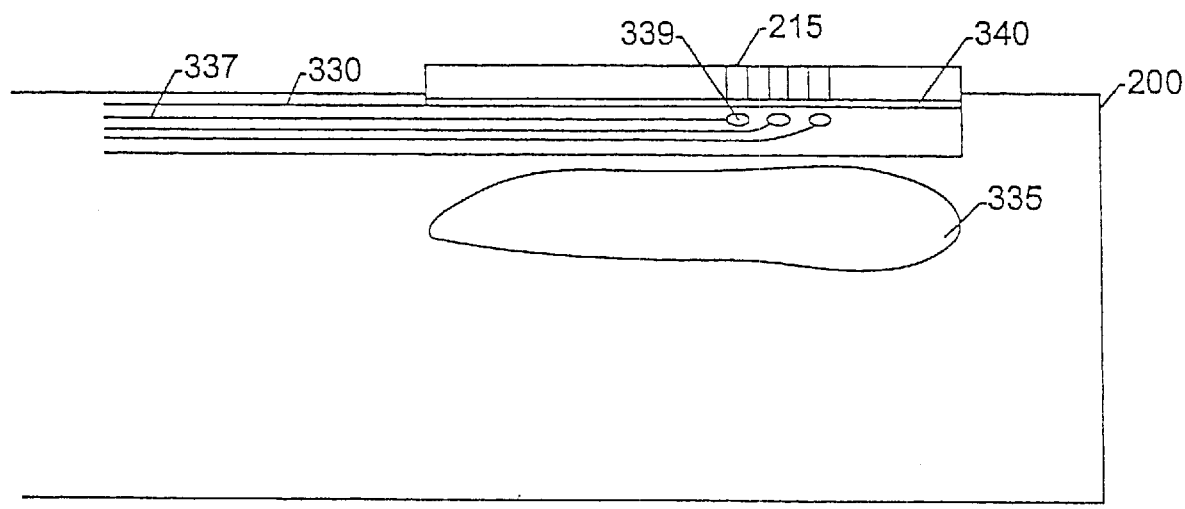
FIG. 3B is an enlarged cross-sectional view of a real time three dimensional imaging probe apparatus configured to emit and receive ultrasonic energy for volumetric side scanning according to the present invention.

FIG. 3B is an enlarged cross-sectional view of a real time three dimensional imaging probe apparatus configured to emit volumetric side scanning ultrasonic energy according to the present invention. A conduit 330 having proximal and distal ends includes a plurality of conductors 337 having proximal and distal ends. The distal end of the conduit 330 is positioned substantially parallel to the ultrasonic transducer phased array 205 to allow a plurality of pads 339, positioned at the distal end of the plurality of conductors 337, to be directly connected to a plurality of corresponding elements of the ultrasonic transducer phased array 205. A backing material 335 is positioned between the conduit 330 and the distal end of the elongated body 210. The backing material 335 is acoustically matched to the mounting plate 305 to reduce the reflection of acoustic energy emitted from the ultrasonic transducer phased array 205. A glue is positioned between the conduit 300 and the ultrasonic transducer phased array 205 to maintian the position of the conduit 300 with respect to the ultrasonic transducer phased array 205. It will be understood that the phrase directly connect, as used herein, includes in contact with and having layers positioned between the mounting plate 305 and the conduit 330.

The conduit 330 can be a Multilayer Flexible Circuit (MFC) that includes the conductors 337 and the pads 339. The conductors 337 can be on the outer surface and the interior of the MFC. The MFC can be oriented within the elongated body to provide a direct connection to the mounting sheet 305. The pads 339 of the MFC are aligned with the elements of the ultrasonic transducer phased array.

Figure 4A:
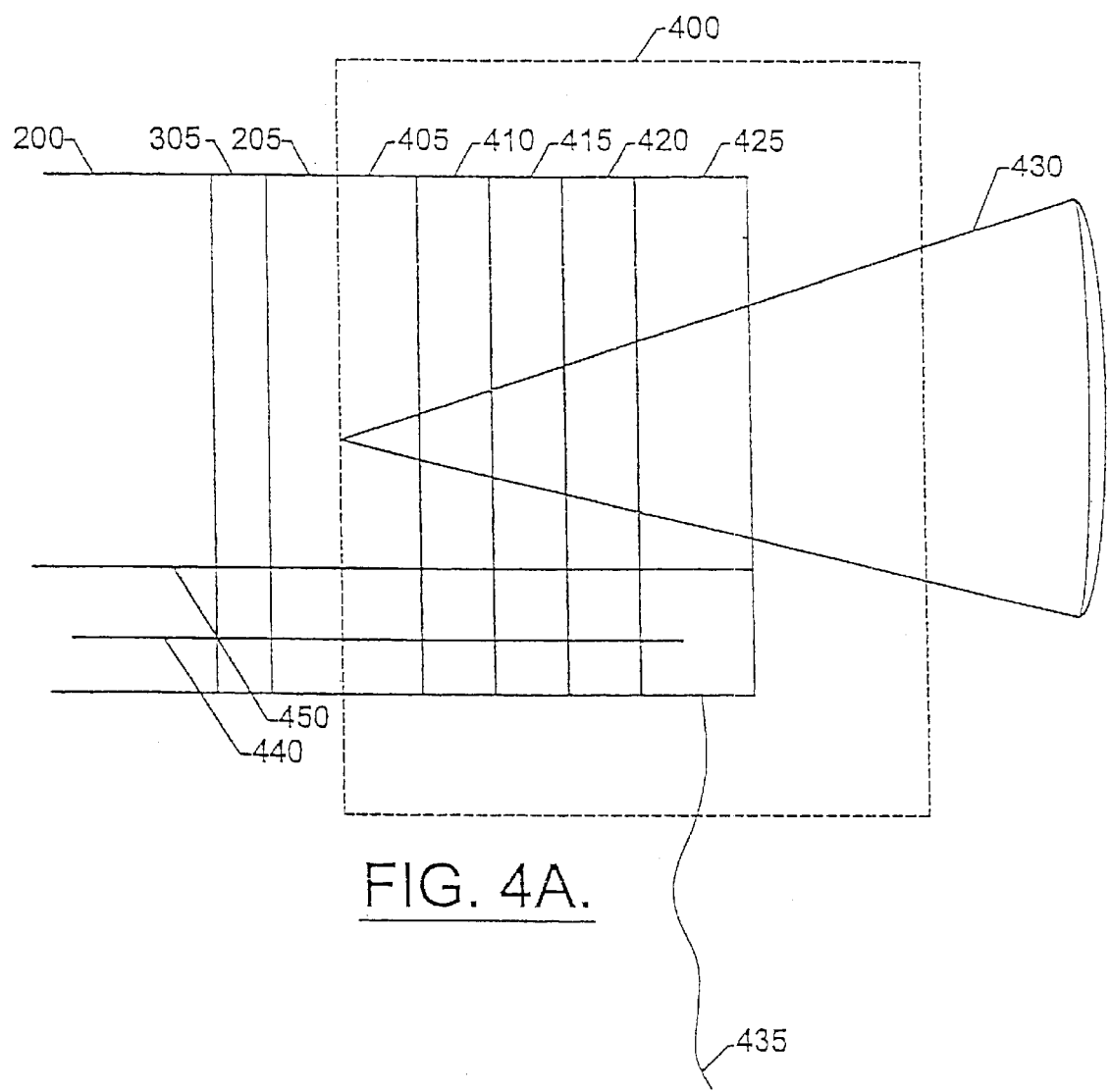
FIG. 4A is an enlarged cross-sectional view of an ultrasonic transducer phased array and electrode according to the present invention.

FIG. 4A is an enlarged cross-sectional view of an ultrasonic transducer phased array 205 and electrode assembly 400 according to the present invention. The ultrasonic transducer phased array 205 is connected to and positioned on the distal end of the elongated body 200 and positioned to emit and receive ultrasonic energy for volumetric forward scanning of objects within the region of interest. The electrode assembly 400 is connected to and overlying the ultrasonic transducer phased array 205. The electrode assembly 400 includes a first ground layer 405 connected to and overlying the ultrasonic transducer phased array 205. The first ground layer 405 can be implemented with a metal layer having a thickness in the range between about 0.02 $\mu$m and 20 $\mu$m. The first ground layer 405 is formed by sputter deposition, plating, a bonded foil, a screen print, or vapor deposition. The first insulator layer 410 is connected to and overlying the first ground layer 405. The first insulator layer 410 is formed from polymide to a thickness in the range between about 0.02 $\mu$m and 20 $\mu$m. The second ground layer 415 is connected to and overlying the first insulator layer 410 and can be implemented with a metal layer having a thickness in the range between about 0.02 $\mu$m and 20 $\mu$m. The second insulator layer 420 is connected to and overlying the second ground layer 415 and can be implemented using polymide formed to a thickness in the range between about 0.02 $\mu$m and 20 $\mu$m. The electrode 425 is connected to and overlying the second insulator layer 420.

As described above, the electrode assembly is transparent to ultrasonic energy. Consequently, the thickness, D, of the electrode assembly 400 does not exceed:

$$D=\lambda$$

where $\lambda$ is the wavelength of the ultrasound energy emitted by the ultrasonic transducer phased array. For example, for ultrasonic energy of 5 MHz, the thickness, D, of the electrode assembly 400 is less than about 0.075 mm.

It should be understood that the phrase connected to, as used herein, includes an arrangement wherein the a first component is physically contacting a second component and an arrangement wherein at least a third component is positioned between the first and second components. Accordingly, the above description includes an arrangement wherein other components are positioned between the ultrasonic transducer phased array 205 and the electrode 425.

The electrode 425 can be used to perform therapy on or monitoring of tissue within the region of interest. For example, the electrode 405 may be an electrocardiogram electrode or electrophysiological mapping electrode used to monitor the activity of heart tissue. Alternately, the electrode 425 can be an ablation electrode used to deliver a stimulus to the tissue within the region of interest. For example, the electrode may be used to deliver a radiofrequency thermal ablation in the range between about 5 Watts to 30 Watts at a frequency in the range between about 300 Hz to 750 kHz.

The position of the electrode 425 connected to and overlying the ultrasonic transducer phased array 205 may provide, in combination with the ultrasonic transparency of the electrode assembly, improved guidance of the electrode to the targeted tissue within the region of interest. The electrode 425 can be positioned by aligning the image with the tissue, thereby possibly reducing complications associated with the alignment of the electrode 425 and the image presented to the user in the prior art. The function of the electrode 425 may be controlled by the controller/signal processor 105 via a guide wire 440 extending through the elongated body 200, through the ultrasonic transducer phased array 205, and through the electrode assembly 400. Alternately, the electrode 425 may be controlled via a wire 435 that is connected to the electrode 425 without passing through the electrode assembly 400. In another embodiment, a fiber optic lead 450 extends through the ultrasonic transducer phased array and the electrode assembly 400. Laser light is emitted from the fiber optic lead to provide therapy to a particular tissue.

Figure 4B:
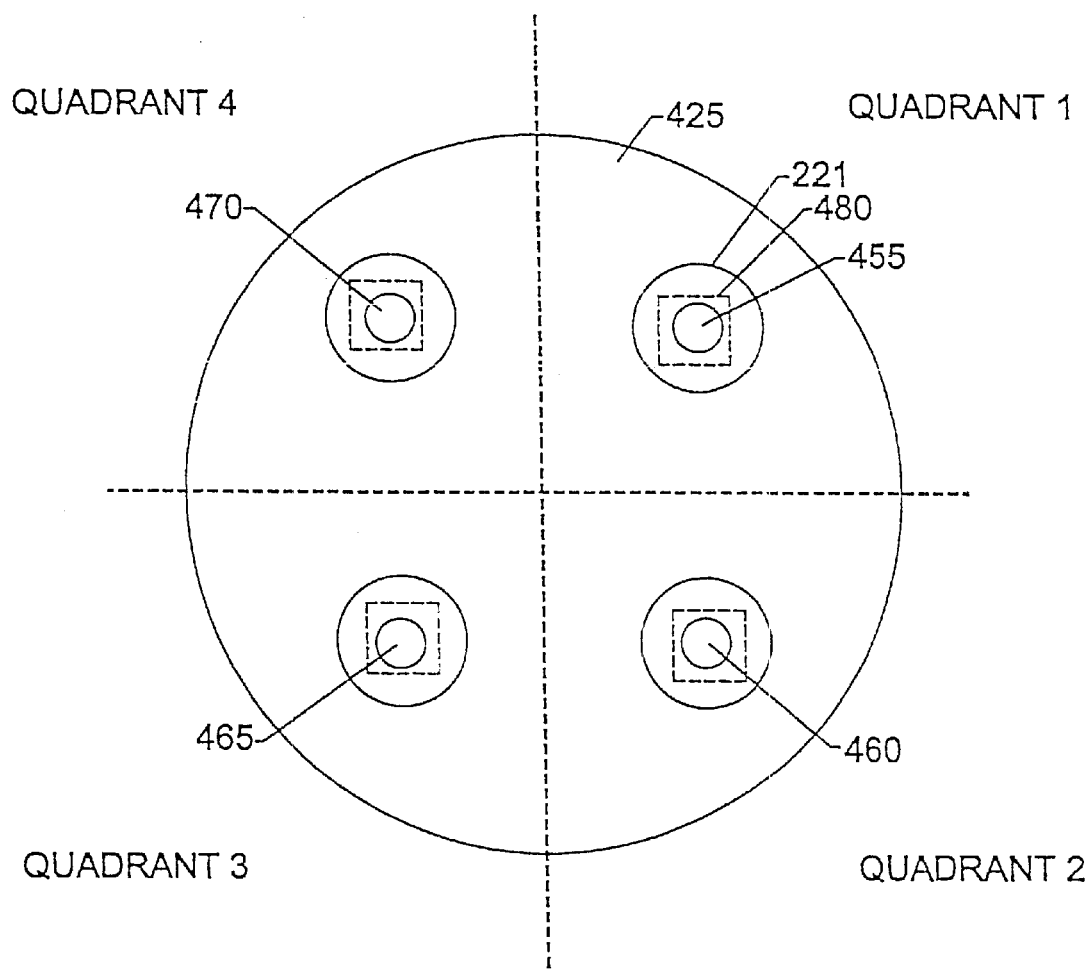
FIG. 4B is an enlarged view of a distal end of an ultrasonic transducer phased array and electrode partially overlying the ultrasonic transducer phased array according to the present invention.

FIG. 4B is an enlarged view of the distal end of an ultrasonic transducer phased array and electrode partially overlying the ultrasonic transducer phased array and tools according to the present invention. The electrode 425 described above, can be used in combination with the tools described herein. The electrode 425 is connected to and overlying the ultrasonic transducer phased array 205. The ultrasonic transducer phased array 205 includes a plurality of sites occupied by ultrasonic transducer elements 215. At least one of the ultrasonic transducer elements 215 is absent from a site, defining an interstitial site 480. A tool 455 is positioned at the interstitial site 480. The electrode 425 does not overlie the tool 455 positioned at the interstitial site 480. The electrode 425, thereby, may not interfere with the operation of the tool. In another embodiment, a plurality of tools 455, 460, 465, and 470 are positioned at a plurality of interstitial sites.

Figure 5A:
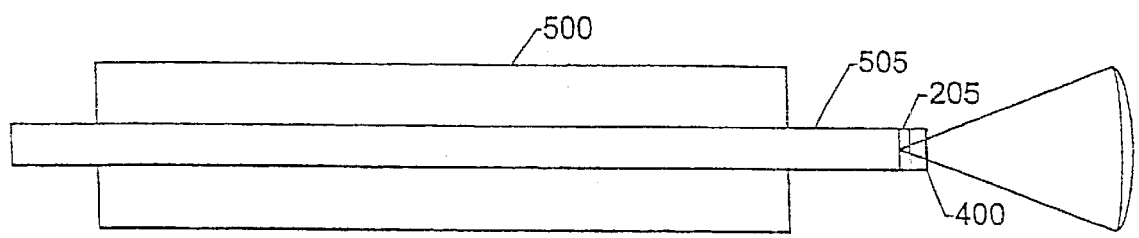
FIG. 5A is a cross-sectional view of a real time three dimensional imaging probe apparatus configured to emit and receive ultrasonic energy for volumetric forward scanning according to the present invention.

FIG. 5A is a cross-sectional view of a real time three dimensional imaging probe apparatus configured to emit and receive ultrasonic energy for volumetric forward scanning according to the present invention. The apparatus shown in FIG. 5A may be used for minimally invasive surgical procedures such as laparoscopic surgery. Laparoscopic surgery may involve the insertion of the cannula 500 through an incision to provide access to a cavity within the body. The cannula 500 provides a surgical port through which tools may access the cavity. The distal end of the elongated body 505 extends through the cannula 500 into the cavity. The ultrasonic transducer phased array 205 is connected to the distal end of the elongated body 505 and is configured to emit volumetric forward scanning ultrasonic energy from the distal end of the elongated body 505 and receive reflected ultrasonic energy.

The present invention provides a three dimensional ultrasonic image of the region of interest to the user, thereby possibly allowing less complicated manipulation of the imaging probe in relation to the tissue. In contrast, the prior art may include a B-mode or slice scanner for surgical procedures of the type described above. The user may therefore need to mentally re-orient the B-mode image to aid in locating and applying the imaging probe.

In one embodiment, tools are combined with the volumetric forward scanning imaging probe as described herein. The ultrasonic transducer phased array 205 includes a plurality sites occupied by a plurality of ultrasonic transducer elements. At least one of the ultrasonic transducer elements is absent from a site, thereby defining an interstitial site. A tool is positioned at the interstitial site.

Figure 5B:
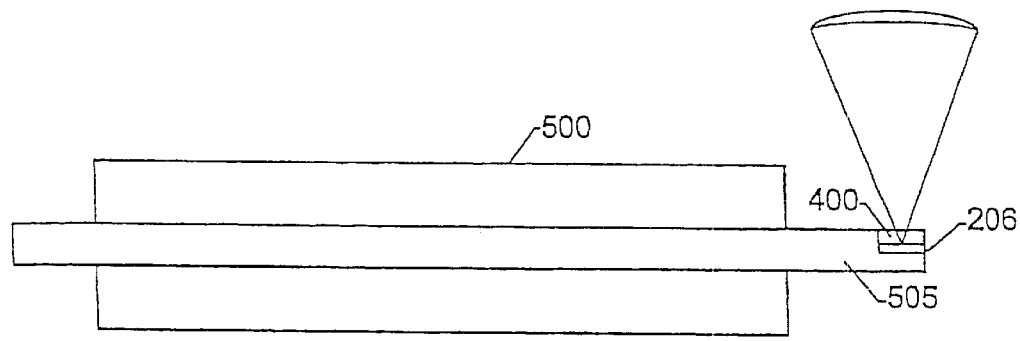
FIG. 5B is a cross-sectional view of a real time three dimensional imaging probe apparatus configured to emit and receive ultrasonic energy for volumetric side scanning according to the present invention.

FIG. 5B is a cross-sectional view of a real time three dimensional imaging probe apparatus configured to provide side scanning ultrasonic energy according to the present invention. Side scanning can provide a real time three dimensional image of objects located such that rotation of a forward scanning probe described above is less practical (such as a cardiac ventricular wall). The ultrasonic transducer phased array 205 is positioned substantially parallel to a longitudinal axis of the elongated body 400 and configured to emit volumetric side scanning ultrasonic energy and receive reflected ultrasonic energy.

In one embodiment, tools are combined with the volumetric side scanning imaging probe described above. The ultrasonic transducer phased array 206 includes a plurality sites occupied by a plurality of ultrasonic transducer elements. At least one of the ultrasonic transducer elements is absent from a site, thereby defining an interstitial site. A tool is positioned at the interstitial site.

Figure 6A:
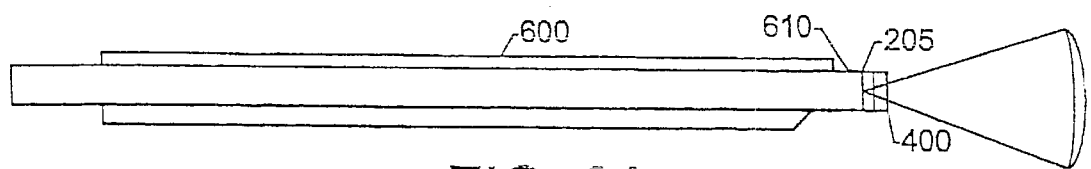
FIG. 6A is a cross-sectional view of a real time three dimensional imaging biopsy apparatus configured to emit volumetric forward scanning ultrasonic energy according to the present invention.

FIG. 6A is a cross-sectional view of a real time three dimensional imaging biopsy apparatus configured to emit volumetric forward scanning ultrasonic energy according to the present invention. The apparatus shown in FIG. 6A may be used for biopsy procedures wherein the biopsy needle 600, having a proximal and distal end, is pointed at the distal end and is configured for insertion into a body. For example, the biopsy needle may have a core element that is removed after insertion into the body. After the core element is removed, the distal end of the elongated body 610 is inserted into the hollow core of the biopsy needle 600 and extended into the body. The ultrasonic transducer phased array 205 is connected to and overlies the distal end of the elongated body 610 and is configured to emit volumetric forward scanning ultrasonic energy.

In one embodiment, tools are combined with the volumetric forward scanning imaging biopsy apparatus as described herein. The ultrasonic transducer phased array 205 includes a plurality sites occupied by a plurality of ultrasonic transducer elements. At least one of the ultrasonic transducer elements is absent from a site, thereby defining an interstitial site.

The present invention provides an ultrasonic transducer phased array 205 to provide the user with images of the region of interest, thereby allowing less complicated manipulation of the biopsy apparatus in relation to the tissue. In contrast, the prior art my include a B-mode or slice scanner for surgical procedures of the type described above. The user, therefore, may need to mentally re-orient the B-mode image to perform the biopsy.

Figure 6B:
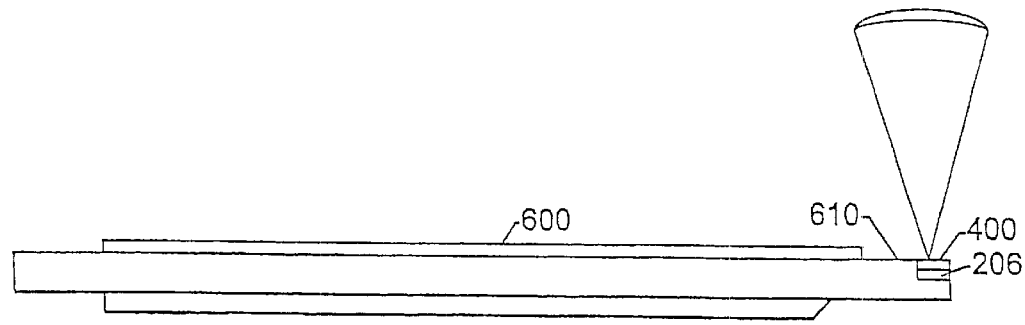
FIG. 6B is a cross-sectional view of a real time three dimensional imaging biopsy apparatus configured to emit volumetric side scanning ultrasonic energy according to the present invention.

FIG. 6B is a cross-sectional view of a real time three dimensional imaging biopsy apparatus configured to provide volumetric side scanning ultrasonic energy according to the present invention. After the core element is removed, the distal end of the elongated body 610 is inserted into the hollow core of the biopsy needle 606 and extended into the body. The ultrasonic transducer phased array 205 is positioned substantially parallel to a longitudinal axis of the elongated body 610 to emit volumetric side scanning ultrasonic energy.

In one embodiment, tools are combined with the volumetric side scanning imaging biopsy apparatus described herein. The ultrasonic transducer phased array 205 includes a plurality sites occupied by a plurality of ultrasonic transducer elements. At least one of the ultrasonic transducer elements is absent from a site, thereby defining an interstitial site. A tool is positioned at the interstitial site. Side scanning can provide a real time three dimensional image of objects located such that rotation of a forward scanning probe described above is less practical (such as a breast tumor).

The imaging probes for biopsy and minimally invasive surgical procedures described herein can exist as unit wherein the components are connected. Alternately, the components may be available as a kit wherein the components are assembled for use. For example, the components can be available as a sterile kit that includes each of the components.

Figure 7A:
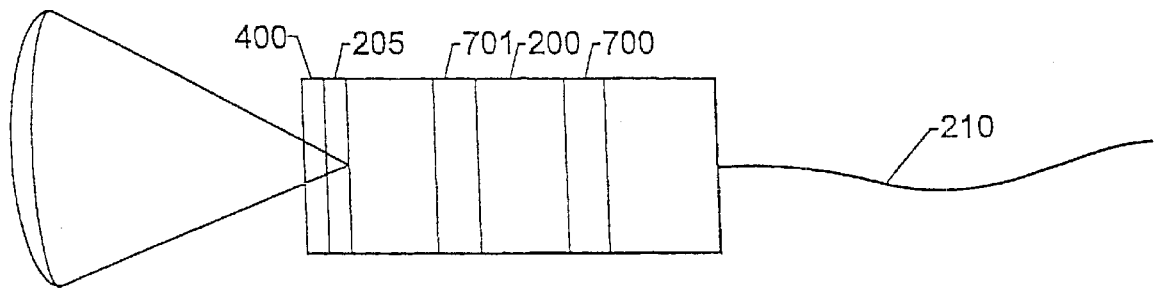
FIG. 7A is an enlarged cross-sectional view of a real time three dimensional catheter apparatus configured to emit and receive ultrasonic energy for volumetric forward scanning and electrodes according to the present invention.

FIG. 7A is an enlarged cross-sectional view of a real time three dimensional imaging catheter apparatus configured to emit volumetric forward scanning ultrasonic energy and an electrode according to the present invention. The catheter shown in FIG. 7A can be used for cardiac diagnosis and treatment by positioning the elongated body 200, having proximal and distal ends, using the three dimensional imaging provided by the ultrasonic transducer phased array 205 that is connected to and overlies the distal end of the elongated body 200. The ultrasonic transducer phased array 205 is positioned to emit volumetric forward scanning ultrasonic energy from the distal end of the elongated body 200. A plurality of electrodes 700 and 701 are connected to and positioned around a perimeter of the elongated body 200 substantially perpendicular to a longitudinal axis of the elongated body 200. Electrodes 700 and 701 can be electrophysiological mapping electrodes used to monitor the tissue in contact with the electrodes 700 and 701. In a preferred embodiment, the electrodes 700 and 701 are positioned around the perimeter of the elongated body 200 so as to provide contact with the tissue regardless of the rotation of the elongated body 200. The electrodes 700 and 701 may also be ablation electrodes that provide therapy to the contacted tissue as described herein.

Figure 7B:
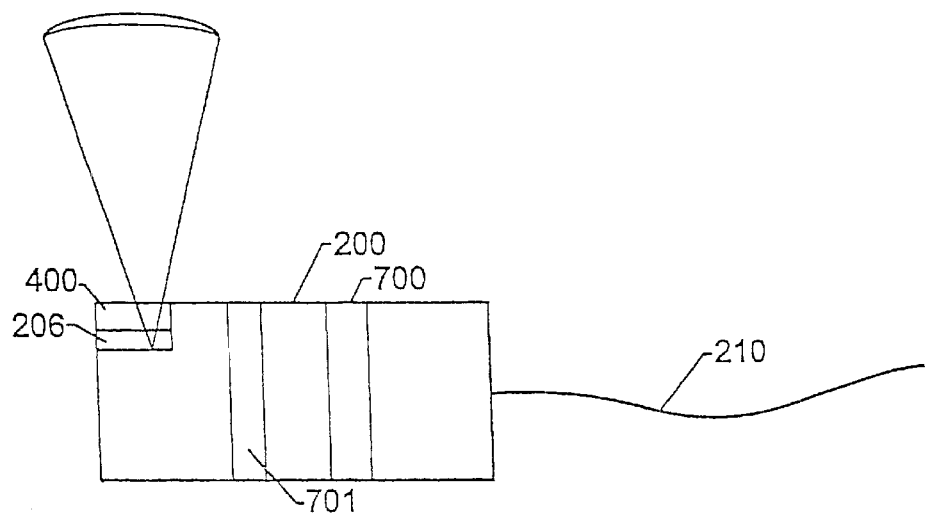
FIG. 7B is an enlarged cross-sectional view of a real time three dimensional catheter apparatus configured to provide side scanning and electrodes according to the present invention.

FIG. 7B is an enlarged cross-sectional view of a real time three dimensional imaging catheter apparatus configured to provide side scanning and an electrode according to the present invention. Side scanning can provide a real time three dimensional image of objects located such that rotation of a forward scanning catheter described above is less practical (such as a cardiac ventricular wall). The apparatus shown in FIG. 7B may be used to locate tissue and apply the electrodes 700 and 701 in areas where the rotation of the imaging catheter of FIG. 7A is impractical.

Figure 7C:
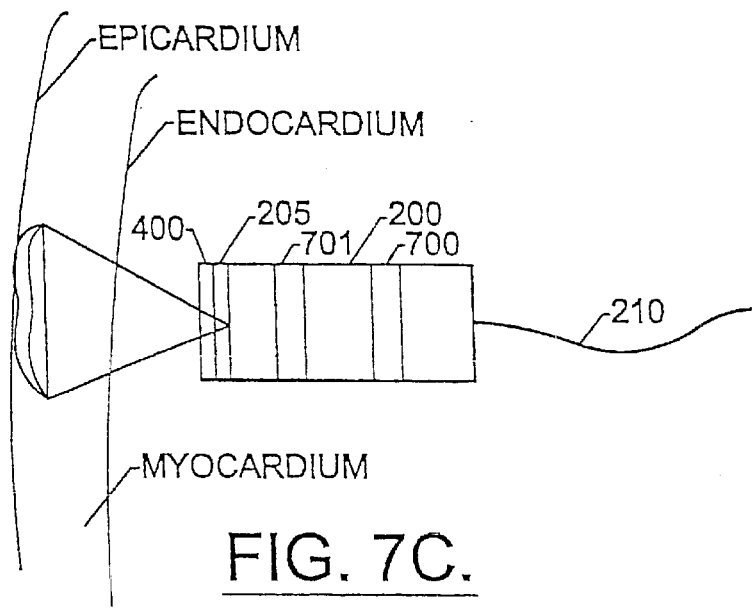
FIGS. 7C and 7D illustrate the use of a real time three dimensional imaging catheter and electrode apparatus of FIG. 7A.
Figure 7D:
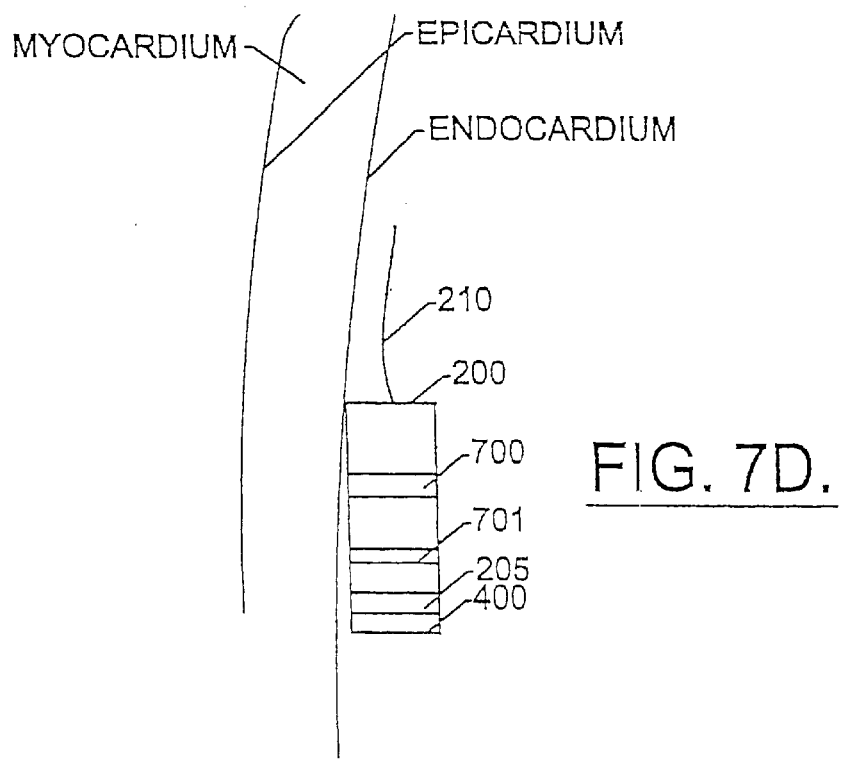

In FIG. 7C, the real time three dimensional imaging catheter apparatus is used locate tissue within the region of interest. In FIG. 7D, the real time three dimensional imaging catheter apparatus is used to monitor the tissue as described above. For example, the volumetric forward scanning ultrasonic catheter may be used to image the endocardium. When the desired tissue is located, the catheter is positioned parallel to the endocardium and the plurality of electrodes are used to treat the located tissue.

The present invention provides volumetric scanning ultrasonic imaging probes and catheters in combination with tools to provide therapy to tissue of interest. In particular, the tool can be a fiber optic lead, a suction tool, a guide wire, an electrophysiological electrode, or an ablation electrode. Positioning the tool at an interstitial site allows a large ultrasonic transducer phased array aperture, thereby producing superior image resolution and sensitivity as compared to the prior art. Positioning the tool within the ultrasonic transducer phased array allows the user to align the tool with the tissue to be treated more accurately, thereby making the probe easier to use and more effective. Conventional probes may include tools, positioned outside the ultrasonic transducer phased array, reducing the aperture size of the ultrasonic transducer phased array. A reduced aperture size provides lower image resolution and sensitivity.

The present invention also provides increased image resolution by increasing the aperture size of the ultrasonic transducer phased array to include a majority of the surface area of the distal end of elongated body. In particular, in contrast to the ultrasonic transducer phased arrays described herein, the ultrasonic transducer phased arrays disclosed in Seward cover a minority of the elongated body described therein. Moreover, Seward discloses an ultrasonic transducer phased array in conjunction with conventional tools and electrodes positioned in close proximity to the ultrasonic transducer phased array, thereby limiting the size of the ultrasonic transducer phased array. As a result, the images produced by the prior art may have low spatial resolution and sensitivity relative to those produced by the present invention.

The present invention also provides improved imaging over the prior art as applied to biopsy and minimally invasive surgical procedures. In particular, the present invention provides a three dimensional ultrasonic image of the region of interest to the user, thereby possibly allowing less complicated manipulation of the electrode assembly in relation to the tissue. In contrast, the prior art may include a B-mode or slice scanner for surgical procedures of the type described above. The user may therefore need to mentally re-orient the B-mode image to aid in locating and applying the electrode assembly.

The present invention also provides real time three dimensional imaging probes with ultrasonically transparent electrodes for use with catheters. The ultrasonically transparent electrode may enable the user to more easily apply the electrode to tissue within a region of interest, thereby allowing a reduction in the complexity associated with the prior art. For example, the present invention may enable the user to apply the electrode to the tissue by locating the tissue within the region of interest using the real time three dimensional images. In contrast, users of imaging probes in the prior art may locate the tissue and then manipulate a tool to the tissue by understanding the registration between the image and the physical location of the electrode on the probe. Moreover, the ultrasonically transparent electrode may reduce the occlusion of the tissue.

In the drawings and specification, there have been disclosed typical preferred embodiments of the invention and, although specific terms are employed, they are used in a generic and descriptive sense only and not for purposes of limitation, the scope of the invention being set forth in the following claims.

What is claimed is:

1. A real time three dimensional ultrasound imaging probe apparatus configured to be placed inside a body, the apparatus comprising:

an elongated body having proximal and distal ends; and a two dimensional (2D) ultrasonic transducer phased array connected to and positioned on the distal end of the elongated body, wherein the 2D ultrasonic transducer phased array is configured to emit ultrasonic energy for volumetric scanning from the distal end of the elongated body and receive reflected ultrasonic energy, and wherein the 2D ultrasonic transducer phased array covers a majority portion of the distal end of the elongated body.

2. A real time three dimensional ultrasound imaging probe apparatus configured to be placed inside a body, the apparatus comprising:

an elongated body having proximal and distal ends;

an ultrasonic transducer phased array connected to and positioned on the distal end of the elongated body, wherein the ultrasonic transducer phased array is configured to emit ultrasonic energy for volumetric scanning from the distal end of the elongated body and receive reflected ultrasonic energy, and wherein the ultrasonic transducer phased array covers a major portion of the distal end of the elongated body;

wherein the major portion of the distal end of the elongated body comprises a first normalized dimension of $(L/\lambda)$ and a second normalized dimension of $(D/\lambda)$;

wherein λ comprises a wavelength of ultrasound energy emitted by the ultrasonic transducer phased array;

wherein L comprises a first aperture size of the ultrasonic transducer phased array in the first dimension; and wherein D comprises a second aperture size of the ultrasonic transducer phased array in the second dimension.

3. An imaging probe apparatus according to claim 1 wherein the 2D ultrasonic transducer phased array comprises a plurality of ultrasonic transducer elements arranged on the distal end of the elongated body to define an octagonal shape.

4. An imaging probe apparatus according to claim 1 wherein the 2D ultrasonic transducer phased array comprises a plurality of ultrasonic transducer elements arranged to define a sparse array of ultrasonic transducer elements.

5. A real time three dimensional ultrasound imaging probe apparatus configured to be placed inside a body the apparatus comprising:

an elongated body having proximal and distal ends;

an ultrasonic transducer phased array connected to and positioned on the distal end of the elongated body, wherein the ultrasonic transducer phased array is configured to emit ultrasonic energy for volumetric scanning from the distal end of the elongated body and receive reflected ultrasonic energy, and wherein the ultrasonic transducer phased array covers a major portion of the distal end of the elongated body; and wherein the ultrasonic transducer phased array comprises a plurality of ultrasonic transducer elements arranged to define a Mills Cross array of ultrasonic transducer elements.

6. A real time three dimensional ultrasound imaging probe apparatus configured to be placed inside a body the apparatus comprising:

an elongated body having proximal and distal ends;

an ultrasonic transducer phased array connected to and positioned on the distal end of the elongated body, wherein the ultrasonic transducer phased array is configured to emit ultrasonic energy for volumetric scanning from the distal end of the elongated body and receive reflected ultrasonic energy, and wherein the ultrasonic transducer phased array covers a major portion of the distal end of the elongated body; and wherein the ultrasonic transducer phased array comprises a plurality of ultrasonic transducer elements arranged to define a random distribution of ultrasonic transducer elements.

7. An imaging probe apparatus according to claim 6 wherein the random distribution of ultrasonic transducer elements comprises a plurality of transmit ultrasonic transducer elements having a gaussian distribution and a plurality of receive ultrasonic transducer elements having a uniform distribution.

8. An imaging probe apparatus according to claim 1 wherein 2D the ultrasonic transducer phased array comprises a plurality of ultrasonic transducer elements arranged to define a periodic distribution of ultrasonic transducer elements in the two dimensions.

9. A real time three dimensional ultrasound imaging probe apparatus configured to be placed inside a body, the apparatus comprising:

an elongated body having proximal and distal ends;

an ultrasonic transducer phased array connected to and positioned on the distal end of the elongated body, wherein the ultrasonic transducer phased array is configured to emit ultrasonic energy for volumetric scanning from the distal end of the elongated body and receive reflected ultrasonic energy, and wherein the ultrasonic transducer phased array covers a major portion of the distal end of the elongated body;

wherein the ultrasonic transducer phased array comprises a plurality of ultrasonic transducer elements arranged to define a periodic distribution of ultrasonic transducer elements; and wherein the periodic distribution of ultrasonic transducer elements comprises a plurality of transmit ultrasonic transducer elements having a first spacing therebetween and a plurality of receive ultrasonic transducer elements having a second spacing therebetween that is different than the first spacing.

10. An imaging probe apparatus according to claim 1 wherein the 2D ultrasonic transducer phased array comprises a plurality of ultrasonic transducer elements that are spaced apart from one another by about 0.2 mm on the distal end of the elongated body.

11. An imaging probe apparatus according to claim 1 wherein the 2D ultrasonic transducer phased array comprises a plurality of first ultrasonic transducer elements arranged to define a first circular pattern and a plurality of second ultrasonic transducer elements arranged to define a second circular pattern outside the first circular pattern and a circular pattern of interstitial sites between the first and second circular patterns.

* * * * *